United States Patent [19]

Omatsu et al.

[11] Patent Number: 4,871,880
[45] Date of Patent: Oct. 3, 1989

[54] HYDROFORMYLATION PROCESS

[75] Inventors: Toshihiro Omatsu; Yasuo Tokitoh; Noriaki Yoshimura, all of Kurashiki, Japan

[73] Assignee: Kuraray Co., Ltd., Kurashiki, Japan

[21] Appl. No.: 198,860

[22] Filed: May 26, 1988

[30] Foreign Application Priority Data

Jul. 22, 1987 [JP] Japan ................................ 62-184135

[51] Int. Cl.$^4$ ............................................. C07L 45/50
[52] U.S. Cl. ........................................ 568/454; 568/451
[58] Field of Search ................................ 568/451, 454

[56] References Cited

U.S. PATENT DOCUMENTS

| | | | |
|---|---|---|---|
| 4,420,640 | 12/1983 | Matsumoto et al. | 568/454 |
| 4,467,116 | 8/1984 | Leeuwen et al. | 568/454 |
| 4,510,332 | 4/1985 | Matsumoto et al. | 568/454 |
| 4,668,651 | 5/1987 | Billig et al. | 568/454 |
| 4,808,737 | 2/1989 | Yoshimura | 549/423 |

FOREIGN PATENT DOCUMENTS

| | | |
|---|---|---|
| 0064285 | 11/1982 | European Pat. Off. . |
| 0094748 | 11/1983 | European Pat. Off. . |
| 0223103 | 5/1987 | European Pat. Off. . |

OTHER PUBLICATIONS

*Chem. Abst.*, vol. 100, No. 21, May 1984, p. 582, Abstract No. 174269t, "1,9-Nonanedial", Kuraray Co., Ltd.

*Primary Examiner*—Werren B. Lone
*Attorney, Agent, or Firm*—Oblon, Spivak, McClelland, Maier & Neustadt

[57] ABSTRACT

A hydroformylation process is provided which comprises reacting a compound of the general formula $$CH_2=CH-CH_2-A-CH_2-X$$

wherein X is a hydroxyl or formyl group and A is a group of the formula $$-(CH_2)_n- \text{ or } -(CH_2)_m-CH=CH-$$

in which n is an integer of 3–8 and m is an integer of 0–5, with a mixture of hydrogen and carbon monoxide in the presence of a rhodium compound and a specific tris(substituted phenyl) phosphite.

8 Claims, No Drawings

HYDROFORMYLATION PROCESS

BACKGROUND OF THE INVENTION

1. Field of the Invention

This invention relates to a hydroformylation process and, more particularly, to a hydroformylation process which comprises reacting a compound of the general formula $$CH_2=CH-CH_2-A-CH_2-X \qquad (I)$$

wherein X is a hydroxyl or formyl group and A is a group of the formula $$-(CH_2)_n- \text{ or } -(CH_2)_m-CH=CH-$$

in which n is an integer of 3–8 and m is an integer of 0–5, with a mixture of hydrogen and carbon monoxide in the presence of a rhodium compound and a specific tris(substituted phenyl) phosphite.

2. Description of the Related Art

It is known that reaction of octa-2,7-dien-1-ol with a mixture of hydrogen and carbon monoxide in an organic solvent in the presence of a rhodium catalyst and a monodentate tertiary organic phosphorus compound such as triphenylphosphine or triphenyl phosphite gives 9-hydroxy-7-nonen-1-al (cf. U.S. Pat. No. 4,420,640). It is also known that hydroformylation of 7-octen-1-al in the presence of a rhodium complex and the sodium, potassium or lithium salt of m-(diphenylphosphino)benzenesulfonic acid gives 1,9-nonanedial (cf. U.S. Pat. No. 4,510,332).

Since rhodium catalysts are very expensive, it is strongly desired from the industrial standpoint that they should be used in quantities as small as possible. However, when the productivity per gram atom of rhodium is low, rhodium catalysts must necessarily be used in increased amounts. From the economical viewpoint, it is therefore required that rhodium catalysts should be recycled repeatedly for a prolonged period of time. The hydroformylation products from the compounds of the above general formula (I) are compounds each having a high boiling point. Thus, for instance, hydroformylation of octa-2,7-dien-1-ol gives 9-hydroxy-7-nonen-1-al and so on as hydroformylation products and hydroformylation of 7-octen-1-al gives 1,9-nonanedial and so on as hydroformylation products. In the process for the production of 9-hydroxy-7-nonen-1-al as desclosed in U.S. Pat. No. 4,420,640, the catalyst activity is not very high and, therefore, use of the rhodium catalyst in relatively high concentrations and recycling and reusing of said catalyst over a long period are desired for carrying out the hydroformylation reaction commercially while maintaining the rate of reaction at sufficiently high levels. However, when the hydroformylation reaction mixture is subjected to distillation for the separation of the high-boiling hydroformylation products, the catalyst in the reaction mixture undergoes thermal degradation and, further, the catalytic activity of the catalyst lowers due to accumulation of high-boiling byproducts. As a result, the cost of catalysts inevitably constitutes a high percentage of the production cost. For avoiding the above problems, U.S. Pat. No. 4,510,332 proposes a method which comprises subjecting the hydroformylation reaction mixture to extraction to thereby separate the catalyst from the reaction product. However, even when this method is emplyed, the rhodium catalyst is required to be present in relatively high concentrations in the reaction system to be carried out at a rate of reaction which is satisfactory from the industrial viewpoint.

On the other hand, U.S. Pat. No. 4,467,116 describes a hydroformylation process which comprises reacting an olefin having a group of the formula

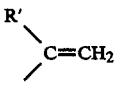

wherein R' is a hydrocarbyl group and the valence bond shown forms part of a hydrocarbyl group or R' together with the valence bond shown represents a ring structure having at least 5 carbon atoms in the ring, for example 2-methyl-1-hexene, limonene or methylenecyclohexane, or an olefin having a group of the formula $$R'-CH=CH-$$

wherein R' is as defined above, for example cyclohexene, with carbon monoxide and hydrogen at a temperature within the range of about 50°–200° C. and a pressure within the range of 2–50 bars in the presence of a hydroformylation catalyst modified with an aromatic phosphite having a specific structure, such as tris(2-t-butylphenyl) phosphite or tris(2-t-butyl-4-methylphenyl) phosphite. However, the above-cited patent specification makes no mention of the applicability of the above hydroformylation process to compounds having an unsubstituted vinyl group and a functional group such as a hydroxyl or formyl group which are other than the olefins having the specific structure mentioned above. Although said specification mentions that there is a vast difference in reactivity between various olefins under similar reaction conditions using an identical catalyst system, this is a well-known fact in the art.

SUMMARY OF THE INVENTION

It is an object of the invention to provide a process for hydroformylating the compounds of the general formula (I) in the presence of low concentrations of a rhodium catalyst at a rate of reaction which is satisfactory from the industrial viewpoint.

Another object of the invention is to provide a hydroformylation process capable of producing branched hydroxyaldehydes or dialdehydes, which are useful as raw materials for the production of polymers, in good yields and in an industrially advantageous manner.

These objects are accomplished by providing a hydroformylation process which comprises reacting a compound of the general formula (I) with a mixture of hydrogen and carbon monoxide in the presence of a rhodium compound and a tris(substituted phenyl) phosphite having an electronic parameter value ($\nu$-value) of 2080°–2090 cm$^{-1}$ and a steric parameter value ($\theta$-value) of 135°–190°.

DETAILED DESCRIPTION OF THE INVENTION

In the above general formula (I), X is a hydroxyl group or a formyl group and A is a group of the formula $$-(CH_2)_n- \text{ or } -(CH_2)_m-CH=CH-$$

in which n is an integer of 3–8 and m is an integer of 0–5.

As examples of the compound of the general formula (I), there may be mentioned octa-2,7-dien-1-ol, 7-octen-1-al, 10-undecen-1-al, 7-octen-1-ol, 8-nonen-1-ol, 9-decen-1-ol and 10-undecen-1-ol, among others.

The terms "electronic parameter value ($\nu$-value)" and "steric parameter value ($\theta$-value)" as used herein are the values defined by C. A. Tolman [Chemical Reviews, 177 (1977), 313]. Thus, the $\nu$-value is defined as the CO stretching frequency of Ni(CO)$_3$L (L being the phosphorus ligand) in the infrared absorption spectrum measured in CH$_2$Cl$_2$ and the $\theta$-value is defined as the apex angle of a cone, centered 2.28 Å from the center of the phosphorus atom, which just touches the van der Waals radii of the outermost atoms of that group which is bonded to the phosphorus atom.

The tris(substituted phenyl) phosphite to be used in accordance with the invention is required to have an electronic parameter value ($\nu$-value) of 2080–2090 cm$^{-1}$ and a steric parameter value ($\theta$-value) of 135°–190°. If at least one of these parameters is outside the above-specified range, such high rate of reaction and such high selectivity toward hydroformylation products as obtainable in accordance with the invention will never be attained.

The tris(substituted phenyl) phosphite to be used in the practice of the invention is selected from among phosphites having the formula P(OR)$_3$ wherein the three Rs are the same or different and each independently represents a substituted phenyl group. The substituent or substituents on the phenyl group may be of any kind provided that they do not interfere with the hydroformylation reaction. Examples of the phosphite which are usable in the practice of the invention are tris(alkyl-substituted phenyl) phosphites such as tris(2-methylphenyl) phosphite, tris(2,6-dimethylphenyl) phosphite, tris(2-isopropylphenyl) phosphite, tris(2-t-butylphenyl) phosphite, tris(2,4-di-t-butylphenyl) phosphite, bis(2-methylphenyl) 2-t-butylphenyl phosphite and bis(2-t-butylphenyl) 2-methylphenyl phosphite; tris(aryl-substituted phenyl) phosphites such as tris(2-phenylphenyl) phosphite; tris(cycloalkyl-substituted phenyl) phosphites such as tris(2-cyclohexylphenyl) phosphite; and tris(alkyl- and halo-substituted phenyl) phosphites such as tris(2-methyl-4-chlorophenyl) phosphite. Among them, tris(2-methylphenyl) phosphite, tris(2,6-dimethylphenyl) phosphite, tris(2-t-butylphenyl) phosphite, tris(2,4-di-t-butylphenyl) phosphite, tris(2-t-butyl-4-methylphenyl) phosphite, tris(2-methyl-4-chlorophenyl) phosphite, tris(2-phenylphenyl) phosphite, tris(2-cyclohexylphenyl) phosphite and the like are preferred because the use thereof can result in successful hydroformylation of the compounds of general formula (I) at a high rate of reaction and with a high selectivity. In particular, tris(2,4-di-t-butylphenyl) phosphite, tris(2-t-butyl-4-methylphenyl) phosphite, tris(2-t-butylphenyl) phosphite, tris(2-cyclohexylphenyl) phosphite and the like are more suited for use in carrying out the process according to the invention. The phosphites may b used either singly or in combination of two or more.

Several typical phosphorus ligands and their $\nu$ and $\theta$ values are shown below in Table A.

TABLE A

| Phosphorus ligand | $\nu$-value (cm$^{-1}$) | $\theta$-value (deg) |
|---|---|---|
| P(C$_6$H$_5$)$_3$ | 2068.9 | 145 |
| P(C$_6$H$_{13}$)$_3$ | 2056.4 | 170 |
| P(2-CH$_3$C$_6$H$_4$)$_3$ | 2066.6 | 194 |

TABLE A-continued

| Phosphorus ligand | $\nu$-value (cm$^{-1}$) | $\theta$-value (deg) |
|---|---|---|
| P(OC$_6$H$_5$)$_3$ | 2085.3 | 128 |
| P(O—2-CH$_3$C$_6$H$_4$)$_3$ | 2084.1 | 141 |
| P(O—2-iso-C$_3$H$_7$C$_6$H$_4$)$_3$ | 2084.6 | 148 |
| P(O—2-C$_6$H$_5$C$_6$H$_4$)$_3$ | 2085.0 | 152 |
| P(O—2-t-C$_4$H$_9$C$_6$H$_4$)$_3$ | 2086.1 | 175 |
| P[O—2,6-(CH$_3$)$_2$C$_6$H$_3$]$_3$ | 2083.2 | 190 |
| P(O—iso-C$_3$H$_7$)$_3$ | 2075.9 | 130 |
| P(O—C$_2$H$_5$)$_3$ | 2076.3 | 109 |
| P[O—2,4-(t-C$_4$H$_9$)$_2$C$_6$H$_3$]$_3$ | 2085.6 | 175 |

From Table A, it is apparent that tris(2-methylphenyl) phosphite, tris(2,6-dimethylphenyl) phosphite, tris(2,4-di-t-butylphenyl) phosphite and the like are phosphites to be preferred in the practice of the invention. It is surprising, however, that such phosphites, in particular tris(2,6-dimethylphenyl) phosphite, are inactive in the hydroformylation of branched olefins having no functional groups, such as 2-methyl-1-hexene (cf. U.S. Pat. No. 4,467,116).

The rhodium compound to be used in the practice of the present invention is a rhodium compound capable of catalyzing the hydroformylation reaction or capable of being converted in the hydroformylation reaction system to a form capable of catalyzing the hydroformylation reaction and includes, to be concrete, rhodium oxide; rhodium chloride; rhodium salts of organic carboxylic acids such as rhodium acetate and rhodium propionate; rhodium carbonyl compounds such as Rh$_4$(CO)$_{12}$, Rh$_6$(CO)$_{16}$ and [Rh(CO)$_2$Cl]$_2$; di-$\mu$-chlorobis(1,3-cyclopentadiene)dirhodium; di-$\mu$-chlorobis(1,5-cyclooctadiene)dirhodium; rhodium acetylacetonate; and rhodium dicarbonyl acetylacetonate. Metallic rhodium carried on active carbon or the like may also be used. Among these, those rhodium compounds which occur in a high valence state can be used after treatment either within or outside the reaction system with an appropriate reducing agent such as carbon monoxide, hydrogen, sodium borohydride or formaldehyde. When such a reducing agent as sodium borohydride is used, the reducing agent may be used in an amount within the range from the stoichiometric amount necessary for the reduction to 5 times as large as said stoichiometric amount. In the process according to the invention, the rhodium compounds show very high catalytic activity and therefore can be used in the reaction mixture in concentrations as low as 0.005–0.1 milligram atom (as rhodium) per liter, preferably 0.01–0.05 milligram atom (as rhodium) per liter.

In accordance with the invention, it is preferable to use the phosphite in an amount of 10–500 moles, more preferably 110–400 moles, per gram atom of rhodium in the rhodium compound. When the phosphite amount is smaller than 10 moles per gram atom of rhodium, the rate of reaction and the selectivity toward the desired hydroformylation products decrease and at the same time the heat stability of the catalyst decreases. Larger amounts than 500 moles rather tend to decrease the rate of reaction and are uneconomical.

In accordance with the invention, the hydroformylation reation is preferably carried out at a temperature within the range of 40°–140° C., more preferably 60°–120° C. At temperatures lower than 40° C., the rate of reaction is low whereas, at temperatures exceeding 140° C., the selectivity toward the desired hydroformylation product decreases. The reaction pressure depends on the reaction temperature employed but, practically, a reaction pressure within the range of about 30–150 atmospheres (absolute), preferably 60–120 atmospheres (absolute), is generally used. Reaction pressures below 30 atmospheres (absolute) are unfavorable since the selectivity of the reaction decreases. Although the reaction can of course be carried out even at a reaction pressure higher than 150 atmospheres (absolute), it is industrially advantageous from the apparatus and procedure viewpoints to maintain the pressure at 150 atmospheres (absolute) or below.

The ratio between the raw material gases, namely hydrogen gas and carbon monoxide gas, when expressed in terms of the mole ratio of hydrogen/carbon monoxide in the feed gas at the entrance into the reactor, is preferably within the range of about 3/1 to 1/3. The simultaneous presence in the reaction system of a gas or gases inert to the hydroformylation reaction in small amounts is allowable. Such inert gases are, for example, methane, ethane, propane, nitrogen, helium, argon, carbon dioxide and dimethyl ether. Although the hydroformylation reaction is desirably carried out in the absence of a solvent, it is also possible to carry out the reaction in the presence of a solvent which is inert within the reaction system. Examples of the solvent are alcohols such as ethanol, butanol, 3-methylbutanol and 3-methylpentane-1,5-diol; saturated aliphatic hydrocarbons such as pentane, hexane, heptane, octane, nonane and decane; aromatic hydrocarbons such as benzene, toluene and xylene; and ethers such as tetrahydrofuran.

In the practice of the invention, it is preferable to add a tertiary organic amine in amounts within the range of 1 mole to 100 moles per gram atom of rhodium to thereby prevent the acetal formation which tends to take place due to trace amounts of acids occurring in the raw materials or formed during the reaction. Examples of the tertiary organic amine which are suited for this purpose are trialkylamines such as triethylamine, tributylamine, tri-n-octylamine and N,N-dimethyl-2-ethylhexylamine; N,N,N',N'-tetraalkyldiaminoalkanes such as N,N,N',N'-tetramethyl-1,2-diaminoethane, N,N,N',N'-tetramethyl-1,3-diaminopropane and N,N,N',N'-tetramethyl-1,4-diaminobutane; tertiary alkanolamines such as N,N-diethylethanolamine and triethanolamine; alicyclic tertiary amines such as N-methylpiperidine, N-methylpyrrolidine and N-methyl morpholine; and pyridines such as pyridine, picoline and lutidine.

When the compounds of general formula (I) in which A is a group of the formula —(CH$_2$)$_m$—CH=CH— (m being as defined above), for example octa-2,7-dien-1-ol, are used in carrying out the hydroformylation reaction according to the invention, it is preferable, for maintaining the selectivity at a high level, to adjust the conversion rate to 90 mole percent or less. At a conversion rate of more than 90 mole percent, a tendency is observed toward rapid increase in the yield of high-boiling by-products resulting from hydroformylation of both the double bonds within the molecule. It is more preferable to maintain the conversion rate within the range of 50–90 mole percent.

The main products can be isolated by subjecting the hydroformylation reaction mixture to distillation, for example at a temperature not higher than 130° C. The rhodium catalyst contained in the distillation residue after distillation at 130° C. or below may be recovered after taking out said residue from the reaction system or may be recycled wholly or partly to the hydroformylation reaction vessel for reuse thereof. In either mode of operation, the process according to the invention can be conducted in an industrially advantageous manner since the rhodium concentration in the reaction system is very low in said process.

The hydroformylation process according to the invention gives, as hydroformylation products, a straight-chain hydroxyaldehyde or dialdehyde (hereinafter referred to as straight-chain product) of the general formula

O=CH—CH$_2$CH$_2$CH$_2$—A—CH$_2$—X   (II)

wherein A and X are as defined above, and a branched-chain hydroxyaldehyde or dialdehyde (hereinafter referred to as branched-chain product) of the general formula

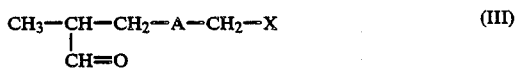

CH$_3$—CH—CH$_2$—A—CH$_2$—X   (III)
　　　|
　　CH=O wherein A and X are as defined above, each resulting from hydroformylation in the terminal olefinic portion of the compound of general formula (I). The process according to the invention gives the straight-chain product and branched-chain product in the form of a mixture thereof. The percentage of the branched-chain product in said mixture generally amounts to about 30–45 mole percent. The straight-chain and branched-chain product mixture obtained by the process according to the invention is useful as a raw material for the production of a mixture of the corresponding straight-chain diol and branched-chain diol, which in turn is useful as a raw material in producing polymers, for example polyesters having good hydrolysis resistance. Thus, when hydrogenated in the presence of a hydrogenation catalyst, the straight-chain and branched-chain product mixture obtained by the process according to the invention gives a mixed diol composed of the corresponding straight-chain diol and branched-chain diol. For example, hydrogenation of the product of hydroformylation of octa-2,7-dien-1-ol or 7-octen-1-al gives a mixture of 1,9-nonanediol and 2-methyl-1,8-octanediol which preferably contains 2-methyl-1,8-octanediol in an amount of not less than 30 mole percent, and this diol mixture is useful as a raw material for the production of polyester diols or polycarbonate diols which are useful for the production of polyurethanes having good low-temperature characteristics and hydrolysis resistance.

Having generally described this invention, a further understanding can be obtained by reference to certain specific examples which are provided herein for the purpose of illustration only and are not intended to be limitative of the scope of this invention unless otherwise specified.

EXAMPLE 1

A catalyst solution was prepared in a 500-ml three-necked flask by dissolving 14.5 mg (0.0562 millimole) of rhodium dicarbonyl acetylacetonate and 10.7 g (22.4 millimoles) of tris(2-t-butylphenyl) phosphite in 300 ml of toluene in an atmosphere of a hydrogen-carbon monoxide mixture (mole ratio 1:1). Then, a 300-ml stainless steel autoclave equipped with a magnetic stirrer was charged, in an atmosphere of a hydrogen-carbon monoxide mixture (mole ratio 1:1), with 10 ml of the above-mentioned catalyst solution and 120 g (0.95 mole) of octa-2,7-dien-1-ol. The rhodium concentration on the rhodium atom basis was 0.0125 milligram atom per liter and the phosphite concentration was 5 millimoles per liter.

Then, the mixture in the autoclave was heated to 100° C. with stirring while the pressure within the autoclave was maintained at 90 atmospheres (absolute) with the same gas mixture as mentioned above. The hydroformylation reaction was then allowed to proceed at 100° C. (inside temperature) for 4 hours. During the reaction, the pressure within the autoclave was always maintained at 90 atmospheres (absolute) by feeding a mixture of hydrogen and carbon monoxide (mole ratio 1:1) through a pressure adjusting valve continuously while the rate of flow of the effluent gas from the autoclave was adjusted to about 5 liters per hour.

After the reaction, the autoclave was cooled, and the reaction mixture (151 g) was taken out.

The reaction mixture obtained was analyzed by gas chromatography. It was found that 0.14 mole of octa-2,7-dien-1-ol remained unreacted. The yields of 9-hydroxy-7-nonen-1-al and 2-methyl-8-hydroxy-6-octen-1-al were 0.43 mole and 0.24 mole, respectively. The conversion of octa-2,7-dien-1-ol was thus calculated to be 85 mole percent, and the selectivities toward 9-hydroxy-7-nonen-1-al and 2-methyl-8-hydroxy-6-octen-1-al were calculated to be 53.1 mole percent and 29.6 mole percent, respectively, on the converted octa-2,7-dien-1-ol basis.

EXAMPLE 2

The procedure of Example 1 was followed except that tris(2,4-di-t-butylphenyl) phosphite was used as the phosphite. Gas chromatographic analysis of the reaction mixture obtained revealed that 0.17 mole of octa-2,7-dien-1-ol remained unreacted and that the yields of the products 9-hydroxy-7-nonen-1-al and 2-methyl-8-hydroxy-6-octen-1-al were 0.42 mole and 0.23 mole, respectively.

The conversion of octa-2,7-dien-1-ol was thus found to be 82 mole percent and the selectivities toward 9-hydroxy-7-nonen-1-al and 2-methyl-8-hydroxy-6-octen-1-al were found to be 53.8 mole percent and 29.5 mole percent, respectively, on the converted octa-2,7-dien-1-ol basis.

EXAMPLE 3

An autoclave was charged with 120 g (0.95 mole) of octa-2,7-dien-1-ol, an amount of $Rh_4(CO)_{12}$ which resulted in a rhodium atom concentration of 0.01 milligram atom per liter, and an amount of tris(2-cyclohexylphenyl) phosphite which resulted in a concentration thereof of 3 millimoles per liter. While the autoclave inside pressure was maintained at 90 atmospheres (absolute) with a mixture of hydrogen and carbon monoxide (mole ratio 2:1), the mixture in the autoclave was heated to 90° C. with stirring. A mixture of hydrogen and carbon monoxide (mole ratio 2:1) was continuously supplied to the autoclave via a pressure adjusting valve so that the pressure could remain constant, while the effluent gas flow rate was adjusted to 10 liters per hour. After 4 hours of reaction, the autoclave was cooled, and the reaction mixture (148 g) was taken out. Gas chromatographic analysis of the reaction mixture revealed that 0.19 mole of octa-2,7-dien-1-ol remained unreacted and that the reaction mixture contained 0.38 mole of 9-hydroxy-7-nonen-1-al and 0.22 mole of 2-methyl-8-hydroxy-6-octen-1-al as products. Thus, the conversion of octa-2,7-dien-1-ol was 80 mole percent and the selectivities toward 9-hydroxy-7-nonen-1-al and 2-methyl-8-hydroxy-6-octen-1-al were 50.0 mole percent and 29.0 mole percent, respectively, on the converted octa-2,7-dien-1-ol basis.

EXAMPLE 4

An autoclave was charged with 64 g (0.51 mole) of octa-2,7-dien-1-ol, 75 ml of toluene, an amount of $Rh_4(CO)_{12}$ which resulted in a rhodium atom concentration of 0.005 milligram atom per liter, an amount of tris(2-t-butyl-4-methylphenyl) phosphite which resulted in a concentration of 1.5 millimoles per liter and an amount of triethanolamine which resulted in a concentration of 2 millimoles per liter.

The mixture was heated to 90° C. with stirring while the autoclave inside pressure was maintained at 60 atmospheres (absolute) with a mixture of hydrogen and carbon monoxide (mole ratio 2:1). The effluent gas flow rate was adjusted to 10 liters per hour and the pressure was kept constant by continuously supplying a mixture of hydrogen and carbon monoxide (mole ratio 2:1) via a pressure adjusting valve.

After 5 hours of reaction, the autoclave was cooled, and the reaction mixture (138 g) was taken out and analyzed by gas chromatography. It contained 0.092 mole of unreacted octa-2,7-dien-1-ol. The contents of the products 9-hydroxy-7-nonen-1-al and 2-methyl-8-hydroxy-6-octen-1-al were 0.22 mole and 0.12 mole, respectively. Thus, it was found that the conversion of octa-2,7-dien-1-ol was 82 mole percent and that the selectivities toward 9-hydroxy-7-nonen-1-al and 2-methyl-8-hydroxy-6-octen-1-al were 52.6 mole percent and 28.7 mole percent, respectively, on the converted octa-2,7-dien-1-ol basis.

EXAMPLE 5

Hydroformylation was carried out under the same conditions as used in Example 2 for 6 hours. Gas chromatographic analysis of the reaction mixture revealed that 0.04 mole of octa-2,7-dien-1-ol remained unreacted and that said mixture contained the products 9-hydroxy-7-nonen-1-al and 2-methyl-8-hydroxy-6-octen-1-al in amounts of 0.34 mole and 0.19 mole, respectively. It was thus found that the conversion of octa-2,7-dien-1-ol was 96 mole percent and that the selectivities toward 9-hydroxy-7-nonen-1-al and 2-methyl-8-hydroxy-6-octen-1-al were 38 mole percent and 21 mole percent, respectively.

EXAMPLE 6

7-Octen-1-al was hydroformylated for 4 hours under the same conditions as used in Example 1 except that 120 g (0.95 mole) of 7-octen-1-al was used in lieu of 120 g of octa-2,7-dien-1-ol. Analysis of the reaction mixture revealed that 0.18 mole of 7-octen-1-al remained unreacted. 1,9-Nonanedial and 2-methyl-1,8-octanedial were found produced in amounts of 0.46 mole and 0.25 mole, respectively. Thus, the conversion of 7-octen-1-al was calculated to be 82 mole percent and the selectivities toward 1,9-nonanedial and 2-methyl-1,8-octanedial were calculated to be 59.7 mole percent and 32.4 mole percent, respectively, on the converted 7-octen-1-al basis.

EXAMPLE 7

Hydroformylation of 10-undecen-1-al was performed under the same conditions as used in Example 1 except that 120 g (0.71 mole) of 10-undecen-1-al was used in lieu of 120 g of octa-2,7-dien-1-ol. After 4 hours of reaction, the reaction mixture was analyzed. There was 0.08 mole of 10-undecen-1-al remaining unreacted. 1,12-Dodecanedial and 2-methyl-1,11-undecanedial were found present in amounts of 0.37 mole and 0.20 mole, respectively. The conversion of 10-undecen-1-al was found to be 88.7 mole percent and the selectivities toward 1,12-dodecanedial and 2-methyl-1,11-undecanedial were found to be 58.7 mole percent and 31.7 mole percent, respectively, on the converted 10-undecen-1-al basis.

COMPARATIVE EXAMPLES 1-4

Octa-2,7-dien-1-ol was hydroformylated in the same manner as in Example 1 except that triphenylphosphine (Comparative Example 1) or triphenyl phosphite (Comparative Example 2) was used in lieu of tris(2-t-butylphenyl) phosphite.

Furthermore, 7-octen-1-al was hydroformylated in the same manner as in Example 6 except that triphenylphosphine (Comparative Example 3) or triphenyl phosphite (Comparative Example 4) was used in lieu of tris(2-t-butylphenyl) phosphite.

The results obtained are shown in Table 1. It is evident that when the rhodium compound concentration is low, the use of an unsuitable phosphorus ligand results in markedly decreased rates of reaction.

TABLE 1

| Comparative Example | Phosphorus ligand | Conversion (mole %) | Selectivity (mole %) | |
|---|---|---|---|---|
| | | | Straight-chain product | Branched-chain product |
| 1 | Triphenylphosphine | 6 | 61[1] | 24[2] |
| 2 | Triphenyl phosphite | 40 | 44[1] | 25[2] |
| 3 | Triphenylphosphine | 6 | 64[3] | 26[4] |
| 4 | Triphenyl phosphite | 35 | 55[3] | 31[4] |

Notes:
[1] The straight-chain product is 9-hydroxy-7-nonen-1-al.
[2] The branched-chain product is 2-methyl-8-hydroxy-6-octen-1-al.
[3] The straight-chain product is 1,9-nonanedial.
[4] The branched-chain product is 2-methyl-1,8-octanedial.

What is claimed is:

1. A hydroformylation process which comprises reacting a compound of the formula $$CH_2=CH-CH_2-A-CH_2-X \quad (I)$$

wherein x is a hydroxyl or formyl group and A is a group of the formula $$-(CH_2)_n- \text{ or } -(CH_2)_m-CH=CH-$$

in which n is an integer of 3-8 and m is an integer of 0-5, with a mixture of hydrogen and carbon monoxide in the presence of a rhodium compound and a tris (substituted phenyl) phosphite having an electronic parameter value ($v$-value) of 2080-2090 cm$^{-1}$ and a steric parameter value ($\theta$-value) of 135°-190°, within the temperature range 40°-140° C. and the pressure range 30-150 atmospheres (absolute).

2. A hydroformylation process as claimed in claim 1, wherein said tris (substituted phenyl) phosphite is tris (2-t-butylphenyl) phosphite, tris (2,4-di-t-butylphenyl) phosphite, tris (2-cyclohexylphenyl) phosphite or tris (2-t-butyl-4-methylphenyl) phosphite.

3. A hydroformylation process as claimed in claim 1, wherein the rhodium compound is used in a concentration on the rhodium atom basis within the range of 0.005-0.1 milligram atom per liter of reaction mixture.

4. A hydroformylation process as claimed in claim 1, wherein the tris(substituted phenyl) phosphite is used in an amount of 10-500 moles per gram atom of rhodium contained in the rhodium compound.

5. A hydroformylation process as claimed in claim 4, wherein the tris(substituted phenyl) phosphite is used in an amount of 110-400 moles per gram atom of rhodium contained in the rhodium compound.

6. A hydroformylation process as claimed in claim 1, wherein the compound of formula (I) is octa-2,7-dien-1-ol.

7. A hydroformylation process as claimed in claim 6, wherein the reaction is performed in a manner such that the conversion of octa-2,7-dien-1-ol does not exceed 90 percent.

8. A hydroformylation process as claimed in claim 1, wherein the compound of formula (I) is 7-octen-1-al.

* * * * *